United States Patent [19]

Fujino

[11] 4,193,408
[45] Mar. 18, 1980

[54] ENDODONTIC THERAPY INSTRUMENT

[75] Inventor: Shoji Fujino, Kita Ooizumi, Japan

[73] Assignee: Shirota Electric Furnace Material Co., Ltd., Tokyo, Japan

[21] Appl. No.: 913,361

[22] Filed: Jun. 7, 1978

Related U.S. Application Data

[63] Continuation-in-part of Ser. No. 751,381, Dec. 17, 1976, abandoned.

[30] Foreign Application Priority Data

Mar. 5, 1976 [JP] Japan .................................. 51/26057

[51] Int. Cl.² ............................................... A61B 5/05
[52] U.S. Cl. ..................................... 128/734; 128/776; 433/27
[58] Field of Search .............. 128/2.1 Z, 2.1 R, 2.1 C, 128/2 S, 734, 735, 776; 32/40 R; 33/174 D

[56] References Cited

U.S. PATENT DOCUMENTS

| | | | |
|---|---|---|---|
| 2,736,313 | 2/1956 | Mathison | 128/2.1Z |
| 3,660,901 | 5/1972 | Inoue | 32/40 R |
| 3,753,434 | 8/1973 | Pike et al. | 128/2.1 Z |
| 3,859,983 | 1/1975 | Dohring et al. | 128/2.1 C |
| 3,894,532 | 7/1975 | Morey | 128/2.1 Z |
| 3,901,216 | 8/1975 | Felger | 128/2.1 Z |
| 3,916,529 | 11/1975 | Mousseau | 128/2 S X |
| 3,993,044 | 11/1976 | McGuffin | 128/2 S |
| 4,016,870 | 4/1977 | Lock | 128/2.1 C |

*Primary Examiner*—Lee S. Cohen

*Attorney, Agent, or Firm*—Schmidt, Johnson, Hovey & Williams

[57] ABSTRACT

An endodontic device for measuring and indicating the depth of penetration of a probe in a root canal of a tooth during a root canal operation includes a meter having a pair of juxtaposed, graduated scales for respectively indicating probe penetration depth in a first broad range of penetration within the root canal, and a second, relatively narrow range of penetration therein, adjacent the apex of the canal, and further includes a bidirectional indicator pointer to provide a precise, accurate visual indication of the probe penetration depth, particularly when such probe is immediately adjacent the apex of the canal. An a.c. measurement signal derived from a d.c. powered oscillator circuit is passed through the probe to a bridge circuit which measures the probe resistance, and thus the position of the probe relative to the canal apex, and also inverts the phase of the measurement signal when the probe reaches a prescribed penetration depth close to the canal apex. A pair of parallel coupled discriminator circuits sense the phase of the measurement signal and are respectively operative to selectively swing the indicator pointer in one direction when the probe is in the first broad penetration range thereof to produce a reading on one of the scales, and reverse the swing direction of the indicator pointer upon sensing a phase change in the measurement signal to produce a reading on the second, expanded scale associated with the second narrow probe penetration range immediately adjacent the canal apex.

10 Claims, 4 Drawing Figures

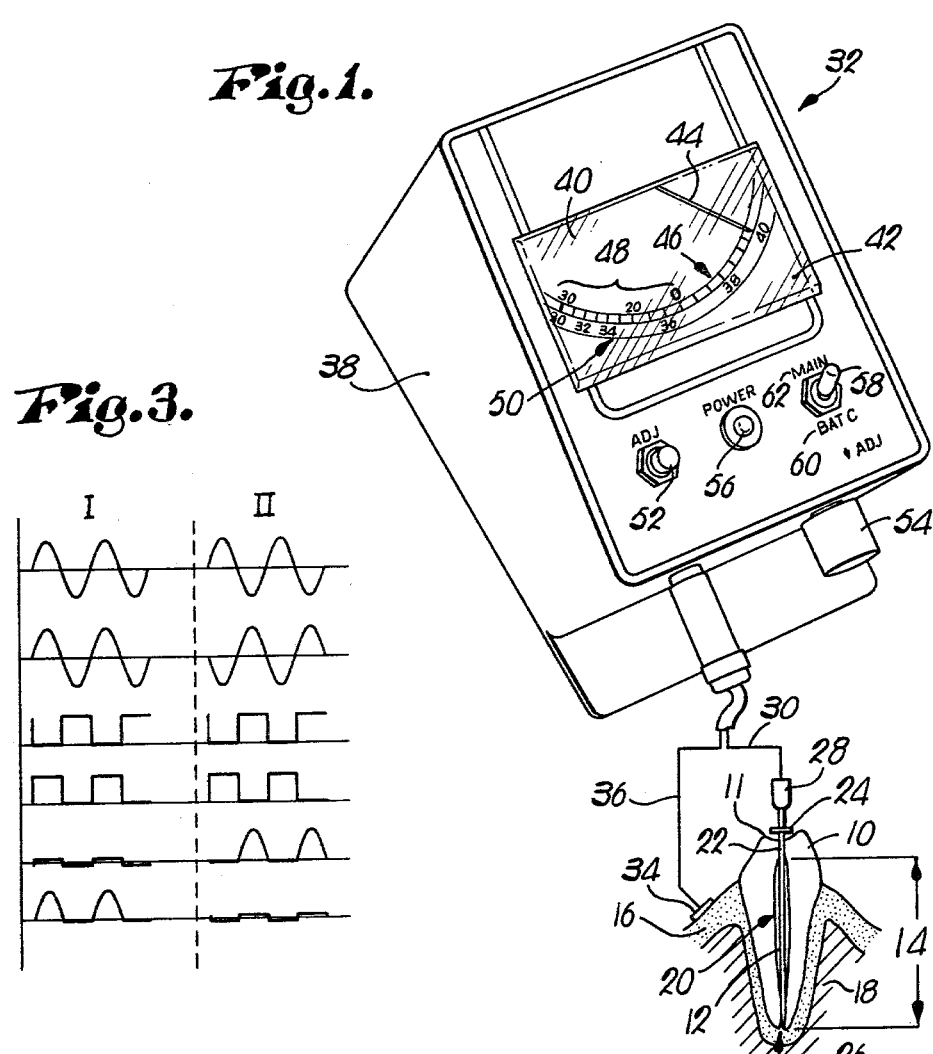
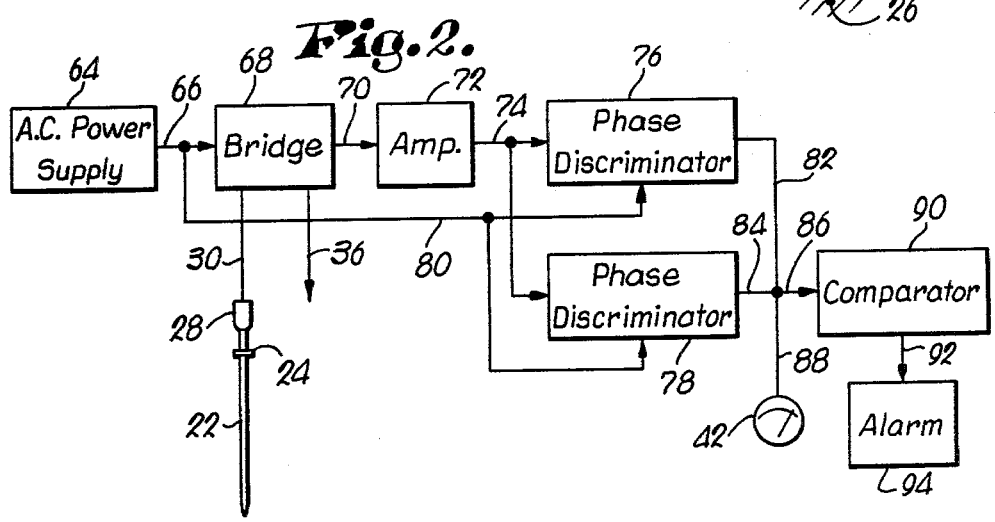

ENDODONTIC THERAPY INSTRUMENT

TECHNICAL FIELD

This is a continuation-in-part of application Ser. No. 751,381 filed, Dec. 17, 1976, now abandoned.

This invention generally relates to endodontic apparatus concerned with measuring and indicating the depth of penetration of a probe such as a reamer in the root canal of a tooth during a root canal operation, and pertains more particularly to a device for measuring the penetration depth of a probe which provides a very precise indication of the penetration depth when the probe is in close proximity to the apex of the canal.

BACKGROUND ART

Conservative dentistry and oral pathology suggest therapeutic treatment of a carious tooth rather than extraction thereof. Consequently, the endodontic treatment technique of root canal operations involving removal of the pulp, treatment of the canal and filling thereof, are being carried out with increasing frequency.

In performing a root canal operation, it is extremely important for the dentist to accurately determine the length of the root canal when removing pulp therefrom and inserting a filling material therein. For instance, if the dentist should fail to reach the apex of the root canal, healthy tissue may be injured or the decayed pulp is allowed to remain which eventually may result in periodontitis or endodontis.

Generally, the endodontic treatment comprises the steps of opening the carious cavity, cutting the enamel caries, removing the coronal pulp, enlarging the root canal orifice, exploring the root canal, extracting the radicular pulp, enlarging the root canal, and filling the root canal. Normally, numerous probe instruments will be employed to perform this treatment method, including cleansers, reamers, files, and filling tools. Heretofore, the most complex, time-consuming and difficult step in the root canal operation has involved determining the depth of penetration of a reamer or file and precisely controlling and limiting the depth of such reamer or file so as not to penetrate either beyond the root apex or short thereof. One previous method of measuring the root canal length involved the insertion of a thin, flexible probe or explorer into the canal and performing x-ray of the carious tooth in order to determine the depth of penetration of the probe into the canal. Once the accurate measurement had been taken, successively used tools could be set to the proper penetration depth determined by the dentist.

Various instruments have been devised in the past for measuring probe penetration in a root canal, as evidenced by the disclosures of U.S. Pats. Nos. 3,916,529; 3,993,044; 3,753,434; 3,894,532; 3,660,901; and, 3,901,216, however, none of the instruments disclosed by such patents has been completely satisfactory in indicating the position of the probe relative to the canal apex with a high degree of sensitivity and accuracy. In this respect, one of the principal of the problems associated with previous instruments relates to the fact that the meters used by such instruments for visually indicating the penetration depth of the probe includes too many graduations to clearly depict the critical point at which the probe actually reaches the canal apex but does not penetrate through such apex inadvertently. In order to overcome the above discussed deficiency, some prior art instruments have provided means for actuating an audible or visual alarm, such as a light, when the probe achieves penetration to a critical point immediately adjacent the apex of the root canal. This solution is unsatisfactory because the dentist is not provided with feedback regarding the rate at which the probe is approaching the apex of the canal and may result in the probe going beyond such apex in the event that the dentist's reaction time after actuation of the alarm is not sufficient to slow or discontinue insertion of the probe after the latter has reached a critical point adjacent the canal apex. Furthermore, the use of audible alarms is undesirable since sounds produced by such alarms may be difficult to distinguish in the case of high ambient background noise.

DISCLOSURE OF INVENTION

It is therefore a primary object of the present invention to provide an improved instrument for automatically treating the root canal with a view toward eliminating the aforementioned defects.

It is another object of the invention to provide an improved device which allows the dentist to locate, visually as well as audibly, the apex of the root canal.

Yet another object of the present invention is to provide an improved device which is capable of carrying out endodontic treatment with minimum interruption to the dentist.

A further object of the present invention is to provide an improved device which employs audible and visual means for reliably indicating the approach of a probe to the apex of a root canal which allows the dentist to concentrate his attention on the performance of the root canal operation so that the latter may be performed in a very safe, fast, and accurate manner.

Still another object of the present invention is to provide an improved device which allows ready interchangeability of probe tools which further contributes to efficiency in performing root canal operations.

Another object of the present invention is to provide an improved device which employs a novel meter having a first graduated scale for indicating probe penetration depths in a first broad range thereof, and a second, larger, expanded graduated scale for indicating probe penetration depths in a second, narrow range thereof adjacent the apex of the canal. As a corollary to the foregoing object, it is a further object of the present invention to provide novel circuitry for measuring the penetration depth of a probe in the canal using an alternating current measurement signal and a bridge circuit for inverting the phase of such signal when the probe is drawn into proximity with the canal apex, along with a pair of discriminator circuits for determining the phase of the measurement signal and for selectively controlling the operation of a meter to indicate the penetration of the probe in either of two separate, discrete ranges of penetration.

These and other objects of the invention are accomplished by providing an improved device for indicating the depth of penetration of a probe in a root canal during a root canal operation.

The invention includes an electrical probe element adapted to be inserted into the root canal which is electrically coupled with a bridge circuit for measuring the changes in resistance in the probe element as the latter is inserted or is withdrawn from the root canal. A d.c. powered oscillator circuit provides an alternating current measurement signal to the bridge circuit which functions to invert the phase of the latter when the resistance of the probe element measured thereby reaches a prescribed value normally corresponding to penetration by the probe element which is relatively close to the apex of the root canal. A pair of parallel coupled phase discriminator circuits operably coupled with the bridge circuit are operative to continuously sense the phase of the measurement signal delivered from the bridge circuit and are selectively operable to produce corresponding output control signals which respectively drive the indicator pointer of a meter in opposite directions to provide scale readings on a pair of corresponding scales to indicate the depth of penetration of the probe element in either of two ranges of penetration. A comparator circuit operably coupled with the output of the phase discriminator circuits is operative to compare the magnitude of the output control signals with a reference value and functions to actuate an audible alarm when the magnitude of one of such control signals exceeds the reference value, thereby indicating that the probe element is in close proximity to, but has not yet reached, a critical penetration point adjacent the apex of the root canal. One of the scales includes expanded graduations whereby to provide significantly improved visual perception of the location of the probe element relative to the critical point immediately adjacent the apex of the root canal.

BRIEF DESCRIPTION OF THE DRAWING

In the drawings:

FIG. 1 is a perspective view of a device for measuring the penetration of a probe in a root canal of a tooth which forms the preferred embodiment of the present invention, a carious tooth being shown in longitudinal section and having the probe of the device inserted therewithin as during the performance of a root canal operation;

FIG. 2 is a combined block and diagramatic representation of the device;

FIG. 3 is a waveform plot wherein the letters A-F represent the waveforms produced by various sections of the circuitry associated with the preferred embodiment, the waveforms in column I and II being respectively related to the condition of the circuitry when the probe is in the first and second penetration ranges thereof.

BEST MODE FOR CARRYING OUT THE INVENTION

Figure 4:
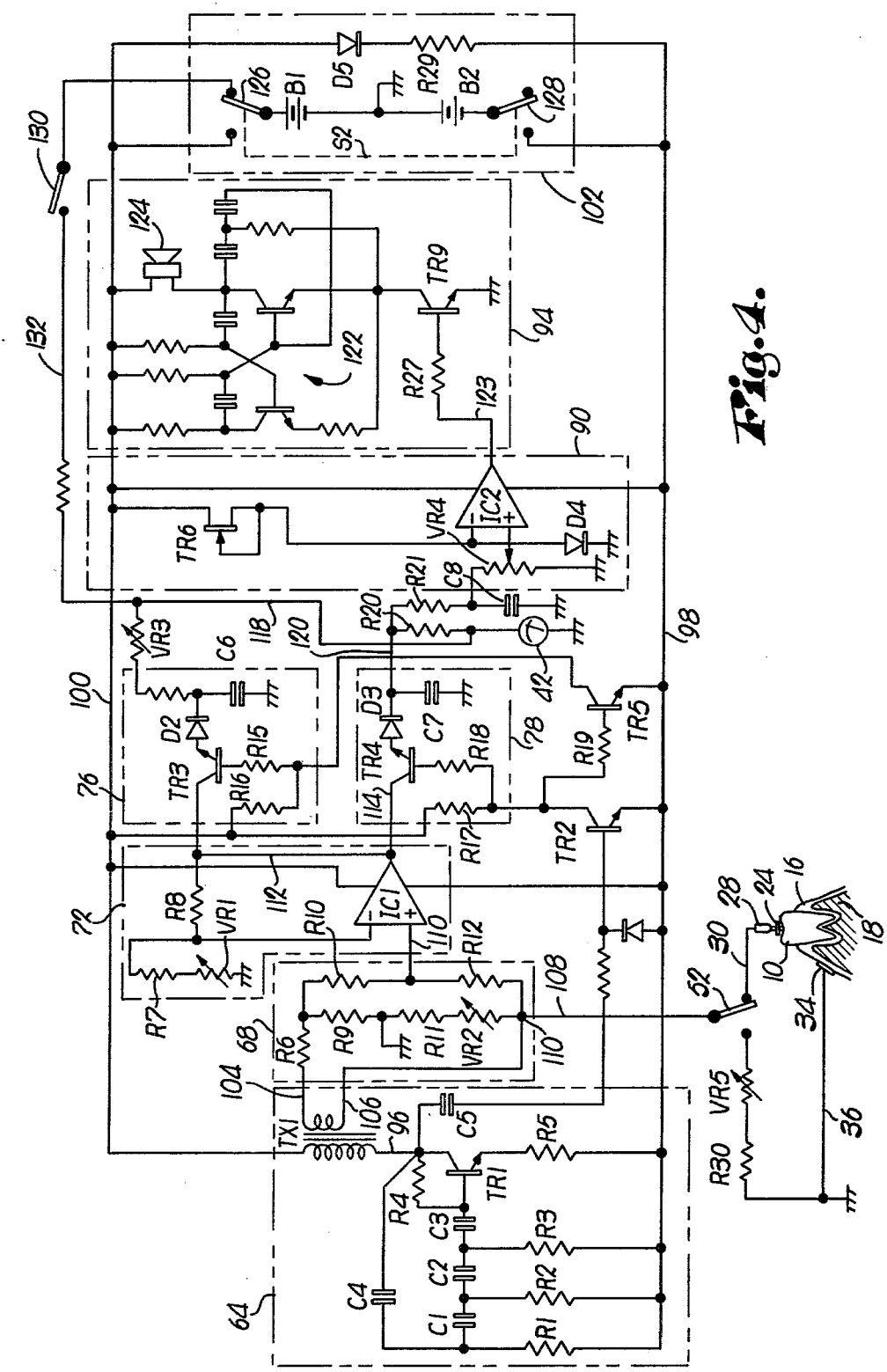
FIG. 4 is a detailed schematic diagram of the circuit for the preferred embodiment of the present invention, the probe thereof being shown in operative relationship to a carious tooth.

Referring first to FIG. 1, a carious tooth 10 upon which a root canal operation is to be performed, includes coronal pulp within the root canal 12 thereof whose length is indicated by the numeral 14. Upper lateral areas of the tooth 10 are surrounded by gingival tissue 16 beneath which the oral mucosa 18 securely holds the tooth 10 in place. Normally, during the course of a root canal operation, the crown 11 of the carious tooth 10 is opened by means of a chisel or bar to remove enamel, thereby providing access to the coronal pulp within the root canal 12. The coronal pulp is then extracted by means of an excavator (not shown) from the tooth 10, after which the root canal orifice indicated by the numeral 20 is enlarged by means of successively inserting into the canal 12 reamers having successively larger diameters until the root canal orifice 20 is of the desired dimension. The probe 22 is provided with a shiftable stop member 24 which may be positioned along the shaft of the probe 22 in a manner which prevents the free tip end of the probe 22 from extending into, or beyond the apex 26 of the root canal 12. Thus, if the length 14 of the root canal is precisely known, the stop member 24 may be adjusted on the probe, and other instruments 22 to prevent the latter from entering, or passing beyond, the apex 26 which may give rise to pulpitis and other inflamation.

The probe 22 is formed of a thin, flexible metal wire which is provided with a head adapted to be carried by a positive holder 28 which electrically couples, in combination with line 30, the probe 22 with the root canal length measuring device, generally indicated by the numeral 32. A negative, or grounded clip 34 is secured to the gingival tissue 16 by any appropriate means, and is operably coupled by line 36 to the device 32.

The device 32 includes a housing 38 adapted to enclose later discussed circuitry and is provided with an opening 40 in the top thereof to allow operator viewing of an ammeter 42 which includes a pivotally mounted, swingable indicator pointer 44. Ammeter 42 further includes an arcuate, composite scale 46 which includes a first set of scale graduations from 0 to 30 microamperes forming a first scale 48 extending from a position centrally located on the composite scale 46 to the left hand side thereof, and further includes a second set of graduations from 30 to 40 microamperes on the lower side thereof which forms a second scale 50 which extends from the left extremity of the scale 46 to the right extremity thereof. A spring biased push button 52 may be operated in conjunction with adjustment knob 54 to slightly adjust the reading of indicator pointer 44. A lamp 56 is provided to indicate when the device 32 is energized, while a switch 58 may be operated between a battery check position 60 and a main position 62 to respectively permit checking the batteries of the device 32 by means of the ammeter 42 and allowing normal operation of the device 32 for measuring the length of a root canal 12 in the tooth 10, or, stated in another manner, for allowing the depth of penetration of the probe 22 in such root canal 12 to be determined.

In use, with the switch 58 in the main position 62 thereof, the indicator pointer 44 normally assumes a centered, intermediate position on the composite scale 46, in alignment with the 0 reading of the first scale 48 prior to the insertion of the probe 22 into the canal 12 of the carious tooth 10. Assuming now that the negative clip 34 is contacting the gingival tissue 16 and that the meter 42 has been adjusted by means of push button 52 and adjustment knob 54, the tip end of the probe 22 is inserted into the orifice 20 of the root. canal 12.

As the probe 22 is inserted into the root canal 12 of the tooth 10, electrical current is allowed to flow from line 30 through the probe 22 to the oral mucosa 18. Initially, just prior to the insertion of the probe 22 into the canal orifice 20 of the tooth 10, there is, of course, no current flow whatsoever from the probe 22 to the oral mucosa 18 inasmuch as the resistance therebetween is infinite. However, as the probe 22 is inserted into the canal orifice 20, the resistance value is gradually reduced as the distance between the tip end of the probe 22 and the apex 26 is decreased. Normally, upon initial insertion of the tip end of the probe 22 into the canal orifice 20, the resistance between such probe 22 and oral mucosa 18 is reduced from infinity to approximately 9 K ohms and such resistance continues to decrease as the tip end of the probe 22 converges toward the apex 26 until such tip actually reaches the apex 26 whereupon the resistance between the probe 22 and the oral mucosa 18 is reduced to approximately 6.35K ohms, which latter mentioned resistance value of 6.35K ohms is the constant resistance value of the oral mucosa 18 of any human body, regardless of the sex, age, etc., of the patient. Thus, for any patient, regardless of the particular tooth upon which a root canal operation is performed, the initial resistance between the probe 22 and the oral mucosa 18 will be approximately 9K ohms and is reduced to approximately 6.35K ohms when the tip end of the probe reaches the apex 26.

As will become clearly apparent hereinafter, novel circuit means are provided for measuring the current flow from the probe 22 through the oral mucosa 18 to the negative clip 34, which current flow is directly related to the change in resistance between the probe 22 and the oral mucosa 18 as the probe 22 is inserted through the root canal 12 of the tooth 10. Prior to the insertion of the probe 22 into the root canal of the tooth 10, the mentioned resistance value will be infinite, consequently the indicator pointer 44 will assume an intermediate position, aligned with the 0 scale graduation on the scale 48 indicating that no current flow is present between the probe 22 and the negative clip 34. Thereafter, as the probe 22 enters the root canal 12 of the tooth 10, the increased current flow from the probe 22 through the oral mucosa 18 to the clip 34 is registered by the ammeter 42, in terms of microamperes, and the indicator pointer 44 swings in a clockwise direction past the 20 microampere scale graduation toward the 30 microampere scale graduation. When the tip end of the probe 22 reaches an intermediate point in the root canal of the tooth 10, the resistance between such probe 22 and oral mucosa 18 will be sufficiently reduced to produce a 30 microampere current flow which is registered by the indicator pointer 44 on the first scale 48. Upon continued penetration by the probe 22 into the root canal of the tooth 10, the direction of movement of the indicator pointer 44 is reversed whereby the latter moves in a counterclockwise direction to produce further scale readings on the second scale 50, which, as can be seen from FIG. 1, includes expanded scale graduations in comparison to the first scale 48, and is provided with scale graduations from 30 to 40 microamperes. As will also be observed from FIG. 1, the scale 50 covers a span of 10 microamperes (from 30 to 40), which is less than half of the 30 microampere span of the scale 48 (from 0 to 30), and the spacing of graduations in at least the higher range part of the scale 50 is at least eight times the spacing of the graduations of the scale 48, for comparable intervals of change in microampere level, both of which contribute to the accuracy of the meter display as the probe 22 more closely approaches the apex 26. When the indicator pointer 44 reaches the 30 microampere scale graduation and reverses its direction of movement to produce scale readings on the second scale 50, the dentist is alerted to the fact that the tip end of the probe 22 is in relatively close proximity to the apex 26 so that further penetration of the probe 22 is performed with increasing caution. As the probe 22 continues to penetrate the root canal 12 of the tooth 10, the pointer 44 swings counterclockwise, as viewed in FIG. 1, and as such pointer 44 passes the 37 microampere scale graduation a later discussed audible alarm is sounded thereby indicating that the tip end of the probe 22 is critically close to the apex 26. The 40 microampere scale graduation on the second scale 50 indicates that the probe 22 has reached the apex 26, and that the next tool should be used by shifting the stop member 24 down along the probe 22 until it rests against the crown 11 of the tooth 10. The depth of the root canal 12 in the tooth 10 can thus be determined by reference to the distance between the stop 24 and the tip end of the probe 22 after the latter has been removed from the tooth.

Referring now also to FIGS. 2 and 3, an alternating current power supply 64 delivers an alternating signal via line 66 to a bridge circuit 68. The bridge circuit 68 is also respectively coupled by lines 30 and 36 to the holder 28 and clip 34. Bridge circuit 68 maintains the mentioned alternating current signal at a relatively low level in order to prevent discomfort to the patient, and 68 further functions to both measure the electrical resistance between lines 30 and 36 and to invert the phase of the mentioned alternating current signal when the electrical resistance between lines 30 and 36 reaches a prescribed value. This phase inversion is evident from FIG. 3 wherein the waveforms on row A represent the alternating current signal delivered on line 66 to the bridge circuit 68, and the waveforms on row B represent the resulting waveform output on line 74 from the amplifier circuit 72, the numerals I and II respectively indicating the state of such waveforms before and after inversion thereof by the bridge circuit 68. Thus, the signal present on line 66 indicated by the waveform in row A in FIG. 3 remains unchanged in columns I and II while the output signal on line 74 indicated by column I, row B in FIG. 3 is identical to the waveform present on line 66 when the magnitude of the mentioned resistance remains above a prescribed value corresponding to scale readings between 0 and 30 microamperes on the first scale 48, but is inverted 180°, as shown in column II, row B of FIG. 3, when the magnitude of such resistance falls below said prescribed value thereof corresponding to scale readings of 30 to 40 microamperes on the second scale 50. From the foregoing, it can be appreciated that the magnitude of the alternating current signal on line 70 is directly proportional to the depth of penetration of the tip of the probe 22 into the root canal 12 of the tooth 10.

The measurement signal present on line 70 is delivered to an amplifier circuit 72 which amplifies such signal and simultaneously delivers such amplified measurement signal on line 74 to first and second phase discriminator circuits 76 and 78 respectively, which are coupled in parallel relationship with each other. As will become apparent hereinafter, the first phase discriminator circuit 76 is operable to allow the ammeter 42 to control the pointer 44 to indicate readings in the 0 to 30 microampere range, while the second phase discriminator circuit 78 is operative to allow the ammeter 42 to control the pointer 44 for indicating readings in the 30 to 40 microampere range. Each of the phase discriminator circuits 76 and 78 have respective second inputs thereto operably coupled by line 80 to line 66. The first phase discriminator circuit 76 is operative to compare the phase of the signal present on line 80 with the signal present on line 74 and delivers a control signal on line 82 only when the phase relationship of the mentioned signals on lines 74 and 80 is identical. The second phase discriminator circuit 78 is also operative to compare the phase relationship of the signals present on lines 74 and 80, and functions to deliver an output signal on line 84 only when the phase relationship of the compared signals on line 74 and 80 are inverted with respect to each other, or stated differently, when such compared signals are 180° out of phase with respect to each other. The cooperative operation of the phase discriminator circuit 76 and 78 is apparent from the waveforms on rows E and F of FIG. 3; upon initial insertion of the probe 22 into the root canal 12, the relatively high resistance value measured by the bridge circuit 68 results in a noninverted alternating current signal being delivered on lines 74 and 80 to both inputs of the first phase discriminator circuit 76, which results in the latter delivering a control signal on line 82 corresponding to the waveform in column I, row F of FIG. 3. However, in the event that the signals on lines 74 and 80 are out of phase with respect to each other, the output of the first phase discriminator circuit 76 is suppressed as shown in column II, row F of FIG. 3. Similarly, when the signals on lines 74 and 80 are in phase with respect to each other, the output of the second phase discriminator circuit 78 on line 84 is suppressed as shown by the waveform in column I, row E of FIG. 3. However, when the resistance measured between lines 30 and 36 drops below the prescribed value thereof, the bridge circuit 68 is operative to invert the alternating current signal on line 66 so that the resulting inverted signals delivered on lines 74 and 80 to the second phase discriminator circuit 78 are 180° out of phase with respect to each other, in which case the second phase discriminator circuit 78 produces an output control signal on line 84 corresponding to the waveform shown in column II, row E of FIG. 3; moreover, when such resistance value drops below the prescribed value thereof, the output of the first phase discriminator circuit 76 is suppressed as shown in column II, row F in FIG. 3. The resulting control signals on lines 82 and 84 are respectively delivered to a comparator 90 and the ammeter 42. From the foregoing then, it is clear at this point that the ammeter 42 selectively receives control signals from either the first phase discriminator circuit 76 or the second phase discriminator circuit 78 to produce corresponding scale readings on the first and second scale 48 and 50 respectively of the ammeter 42.

Comparator 90 is operative to compare the magnitude of the current present on line 86 with a prescribed value thereof and functions to deliver an output signal on line 92 to an alarm circuit 94 for audibly indicating to the dentist that the probe 22 is in close proximity to the apex 26; in the preferred embodiment disclosed herein, the comparator 90 will deliver an output signal on line 92 when the current on line 86 reaches 37 microamperes on scale 50 of the ammeter 42.

Turning attention now to FIG. 4, the alternating current power supply indicated within the broken line 64 includes a phase-shift oscillator comprising resistors R1-R5, capacitors C1-C5 and transistor TR1 which produces a sinusoidal voltage signal that is delivered on line 96 to one side of a low frequency transformer TX1. The above mentioned phase-shift oscillator receives a direct current voltage on lines 98 and 100 from a direct current power supply generally indicated within the broken line 102, which power supply 102 comprises batteries B1 and B2 which may be selectively coupled into parallel relationship with diode D5 and resistor R29, and into series relationship with lines 98 and 100 by means of the double pole, double throw switch S2. The alternating current signal produced by power supply 64 is coupled by transformer TX1 and lines 104 and 106 to an ordinary wheatstone bridge circuit, generally indicated within the broken line 68, which comprises resistors R9, R10, R12, in three respective "legs" of such bridge circuit, while resistor R11 and variable resistor VR 1 are connected in the fourth leg of the bridge circuit 68. The root canal resistance to be measured on line 30 is coupled through the single pole, double throw push button switch 52, and line 108 to terminal 110, thus it can be appreciated that the root canal resistance on line 30 to be measured is coupled in parallel relationship with the leg of the bridge circuit 68 containing resistor R11 and variable resistor VR2, with respect to ground.

The values of the various components comprising the bridge circuit 68 are selected in a manner to produce balancing of the bridge circuit 68 when the root canal resistance on line 30 reaches approximately 16.5 K ohms; consequently, those skilled in the art can readily appreciate that the phase of the alternating current signal output from the bridge circuit 68 on line 110 remains unchanged from the phase of such signal on lines 104 and 106 when the resistance measured on line 30 is between 16.5 K ohms and infinite, but is inverted when such measured resistance on line 30 is between 0 and 16.5 K ohms. Upon operation of the push button switch 52 to connect line 108 with variable resistor VR2, the full scale reading of the pointer 44 of the ammeter 42 may be calibrated. The output of the bridge circuit 68 on line 110 is delivered to the input of an amplifier circuit generally indicated within the broken line 72 which comprises a conventional integrated circuit amplifier IC1, along with resistors R7 and R8 as well as the variable resistor VR1. More particularly, the input from the bridge circuit 68 on line 110 is delivered to the positive input of integrated circuit IC1, the output of the amplifier circuit 72 being respectively simultaneously delivered by lines 112 and 114 to the inputs of first and second phase discriminator circuits generally indicated within the broken lines 76 and 78. The gain of amplifier IC1 may be adjusted by means of the variable resistor VR1 which is operably coupled with the negative input of such amplifier. Discriminator circuit 76 comprises transistor TR3 whose base is coupled to line 100 through resistor R16 as well as to the collector of transistor TR5 via line 116 and resistor R15. The emitter of transistor TR3 is coupled through diode D2 to the variable resistor VR3 as well as to ground through capacitor C6, the collector of transistor TR3 being coupled to the output of the amplifier circuit 72 by line 112. Phase discriminator circuit 78 comprises a transistor TR4 whose base is coupled by resistor R17 to line 100 as well as to the collector of transistor TR2 through resistor R18, the emitter of transistor TR4 being coupled by diode D3 to ground via capacitor C7 as well as to the ammeter 42 through resistor R20. The collector of transistor TR4 is coupled by line 114 to the output of amplifier circuit 72.

Transistors TR2 and TR5 respectively function to control the phase discriminator circuit 76 and 78, and act as inverters of the output of the power supply 64 whereby to produce outputs therefrom respectively on the positive and negative half cycles of the output of the amplifier circuit 72. As shown in FIG. 3, the output of transistor TR5 shown on row D remains in phase with the output of the power supply 64 shown on row A, even when a phase change is produced by the bridge circuit 68. Similarly, the output of transistor TR2 shown on row C is inverted with respect to the output of the power supply 65 shown on row A, and remains inverted in spite of phase changes produced by the bridge circuit 68. Diodes D2 and D3 respectively associated with the phase discriminator circuit 76 and 78 each function to allow an output from the respectively associated phase discriminator circuit only on a positive half cycle of the output voltage delivered from amplifier circuit 72, corresponding to the waveforms shown on row B in FIG. 3. Consequently, transistor TR3 produces a sine wave output only when transistor TR5 produces output pulses, while diode D2 functions to halfway rectify the resulting sine wave output from TR3 so that the output delivered from the phase discriminator circuit 76 through variable resistor VR3 on line 118 to the ammeter 42 corresponds to the waveforms shown on row F of FIG. 3; from the waveforms shown on line F, it can be appreciated that the ammeter 42 receives a halfway rectified sinusoidal signal which is in phase with the output of the power supply 64 as long as the output signal from the amplifier circuit 72 is non-inverted, as shown in column I of row B of FIG. 3. However, upon inversion of the output signal from the amplifier circuit 72 produced by the bridge circuit 68, as shown in column II, row B of FIG. 3, the phase discriminator circuit 76 fails to produce any output signal whatsoever, as may be seen on row F in column II. Conversely, the square wave output of transistor TR2 is normally inverted with respect to the output of the power supply 64 as indicated on row C, column I of FIG. 3, consequently the resulting output from the phase discriminator circuit 78 is suppressed as shown on row E, column I. However, as the measured resistance between lines 30 and 36 gradually decreases and falls below the 16.5 K ohm level, bridge circuit 68 inverts the phase of the output from the power supply 64 so that the phase of the amplifier circuit 72 is likewise inverted thereby placing the square wave output of transistor TR2 in phase with the output of amplifier circuit 72; under these conditions the phase discriminator circuit 78 produces a half wave rectified sinusoidal signal, as shown on row E, column II of FIG. 3, which is delivered on line 120 through resistor R20 to the ammeter 42. It is apparent at this point then, that the pointer 44 of the ammeter 42 is made to swing in opposite directions and is respectively controlled by the outputs of phase discriminator circuits 76 and 78 operating in cooperation with transistors TR5 and TR2.

The output of phase discriminator circuit 78 is delivered via line 120 through a low pass filter consisting of resistor R21 and capacitor C8, and through the variable resistor VR4 to the positive input of an integrated circuit amplifier IC2 which is employed as a comparator in the present circuit. The negative input to comparator IC2 is operably coupled to a constant reference voltage circuit which comprises diode D4 and a field effect transistor TR6 whose gate terminal is operably coupled with the source terminal thereof to form a constant current circuit. Comparator IC2 in combination with variable resistor VR4, field effect transistor TR6 and diode D4 form in combination, the comparator circuit 90. When the voltage on the positive terminal of comparator IC2 exceeds the reference voltage applied to the negative terminal thereof, the comparator IC2 produces an output signal which is delivered to the alarm circuit generally indicated within the broken line 94 which comprises resistor R27, transistor TR9, astable multivibrator oscillator 122 and speaker 124. Upon receipt of the output signal from comparator IC2 on line 123 at the base of transistor TR9, the latter is turned on thereby activating the oscillator 122 which in turn energizes speaker 124 that sounds an audible alarm to alert the dentist to the fact that the tip of the probe 22 is critically near the apex of the root canal 12; normally this will occur when the pointer 44 is approximately aligned with the 37 or 38 microampere scale reading on the scale 50. However, the particular scale reading at which the speaker 124 is energized may be varied by adjusting the variable adjuster VR4, which in turn changes the point at which the comparator IC2 produces an output signal therefrom.

In passing, it is to be noted that with switch poles 126 and 128 in the position shown in FIG. 4, upon closing the switch 130, the ammeter 42 is coupled by line 132 to batteries B1 and B2 thereby allowing the pointer 44 to indicate the strength of the charge on batteries B1 and B2.

From the foregoing, it is clearly apparent that the invention is well adapted to indicate the penetration of the probe 22 into the root canal 12 of the tooth 10 with a high degree of accuracy, and in a manner which allows the dentist to visually confirm the rate at which the tip of the probe is approaching the apex 26 of the root canal 12.

INDUSTRIAL APPLICABILITY

The details of the construction and industrial application of the invention have been made amply clear by the previous description thereof. It is apparent from the foregoing, that the dentist can perceive the approach of the probe 22 to the root apex 26 not only by viewing the reading on the ammeter 42 but by also listening to the alarm, thereby always assuring that the tip of the probe 22 precisely reaches, but does not overshoot the root apex 26. After reaching the root apex 26 with the probe 22, the dentist can determine the actual distance between the stop 24 and the apex 26 and may then proceed with subsequent use of tools such as a reamer, cleanser, or filler, by relying on the initially measured root canal distance 14.

It is submitted therefore, that a simple, compact, yet efficient and useful method in instrument for ascertaining the correct depth of penetration in a root canal has been discovered and, furthermore that the device disclosed is adapted to be used with equal facility in connection with either the interior or posterior teeth.

While a full and complete description of the invention has been set forth in accordance with the dictates of the patent statutes, it is apparent that modifications may be resorted to without departing from the spirit hereof or the scope of the appended claims.

I claim:

1. A device for measuring penetration into a root canal of a tooth, including:
   an electrically conductive probe;
   means operably coupled with said probe for producing an electrical measurement signal corresponding to the penetration of said probe in said canal;
   meter means for measuring the penetration of said probe in said said canal,
   said meter means including an electrically responsive, shiftable indicator, and first and second graduated scales operatively associated with said indicator for respectively displaying the penetration of said probe in first and second ranges in said canal, said second range of penetration being smaller than said first range thereof, said second scale having the graduations thereof expanded whereby to enhance the accuracy of displaying the penetration of said probe in said second range thereof; and electrical circuit means operably coupled with said signal producing means and with said meter means, for operating on said measurement signal to selectively generate and apply to said meter means first and second control signals respectively corresponding to the penetration of said probe in said first and second ranges thereof in said canal, said first control signal being operable for producing shifting of said indicator in one direction to display the penetration of said probe in said first range thereof on said first scale, said second control signal being operable for producing shifting of said indicator in another direction to display the penetration of said probe in said second range thereof on said second scale.

2. The invention of claim 1, wherein:

said measurement signal includes an alternating waveform component and said signal producing means includes oscillator means for generating alternating current signals, and said circuit means includes means for measuring the resistance of said probe and for changing the phase of said measurement signal when the resistance of said probe falls below a prescribed value corresponding to penetration by said probe into said second range thereof.

3. The invention of claim 2, wherein said circuit means further includes means for sensing the phase of said measurement signal and for selectively producing said first and second control signals in accordance with the phase of said measurement signal sensed thereby.

4. The invention of claim 3, wherein said phase sensing means includes:

a first phase discriminator circuit means operative to produce said first control signal therefrom only when the phase of said measurement signal remains unchanged by said resistance measuring and phase changing means, and a second phase discriminator circuit means operative to produce said second control signal therefrom only when the phase of said measurement signal is changed by said resistance measuring and phase changing means.

5. The invention of claim 4, wherein said first and second phase discriminator circuit means each include a transistor operably coupled with a diode.

6. The invention of claim 4, wherein said resistance measuring and phase changing means includes a bridge circuit having a resistive element operably coupled in each circuit arm thereof, and said first and second phase discriminators circuit means are coupled between said bridge circuit and said meter means.

7. The invention of claim 6, wherein there is further provided:

comparator circuit means operably coupled with said second phase discriminator circuit means for comparing the magnitude of said second control signal with a reference value, said comparator circuit means being further operative to produce an output signal therefrom when the magnitude of said second control signal exceeds said reference value; and means operably coupled with said comparator circuit means and under control of the latter for producing an alarm upon receipt thereby of said output signal from said comparator circuit means.

8. The invention of claim 1, wherein:

said indicator is pivotally mounted on said meter means for swinging movement between an intermediate position and first and second full scale positions on respective opposite sides of said intermediate position thereof, said indicator being responsive to said first control signal to swing from said intermediate position thereof in said one direction to said first full scale position, and being further responsive to said second control signal to swing from said first full scale position in said another direction past said intermediate position thereof to said second full scale position thereof.

9. The invention of claim 1, wherein the span of values represented by said graduations of said second scale associated with the penetration of said probe in said second range thereof is less than one half the span of values represented by the graduations of said first scale associated with the penetration of said probe in said first range thereof.

10. The invention of claim 9, wherein at least certain of said graduations of said second scale are expanded at least eight times with respect to said graduations of said first scale.

* * * * *